United States Patent [19]

Kuhla et al.

[11] Patent Number: 4,748,164

[45] Date of Patent: May 31, 1988

[54] BICYCLIC BENZONOID ALKYLENE AMINO THIENO [3,4-D] ISOTHIAZOLE ETHERS AND THIOETHETHERS, PHARMACEUTICAL COMPOSITIONS AND USE

[75] Inventors: Donald E. Kuhla, Doylestown; Henry F. Campbell, Lansdale; William L. Studt, Harleysville, all of Pa.

[73] Assignee: Rorer Pharmaceutical Corporation, Fort Washington, Pa.

[21] Appl. No.: 104,849

[22] Filed: Oct. 5, 1987

Related U.S. Application Data

[60] Division of Ser. No. 878,284, Oct. 22, 1985, Pat. No. 4,699,906, which is a continuation-in-part of Ser. No. 664,222, Oct. 24, 1984, Pat. No. 4,588,719, which is a continuation-in-part of Ser. No. 604,813, Apr. 27, 1984, Pat. No. 4,638,001, which is a continuation-in-part of Ser. No. 489,702, Apr. 29, 1983, Pat. No. 4,529,723.

[51] Int. Cl.⁴ .................. A61K 31/425; A61K 31/535; C07D 513/04

[52] U.S. Cl. .................... 514/212; 514/253; 514/256; 514/321; 514/373; 514/234.2; 514/228.5; 540/603; 544/58.7; 544/133; 544/333; 544/368; 546/198; 548/212

[58] Field of Search ............... 540/603; 544/58.7, 133, 544/333, 368; 546/198; 548/212; 514/212, 222, 229, 253, 256, 321, 373

[56] References Cited

U.S. PATENT DOCUMENTS 4,490,527  12/1984  Schiehser et al. ................... 548/212

*Primary Examiner*—Robert W. Ramsuer
*Attorney, Agent, or Firm*—James A. Nicholson; Alexis Barron; Martin F. Savitzky

[57] ABSTRACT

A class of bicyclic benzenoid aminoalkylene ether and thioether compounds exhibiting pharmacological activity, including anti-secretory and anti-ulcero-genic activity, pharmaceutical compositions comprising these compounds, and methods for the treatment of gastrointestinal hyperacidity and ulcerogenic disorders in mammals using said compositions.

9 Claims, No Drawings

BICYCLIC BENZONOID ALKYLENE AMINO THIENO [3,4-D] ISOTHIAZOLE ETHERS AND THIOETHETHERS, PHARMACEUTICAL COMPOSITIONS AND USE

This application is a divisional of application Ser. No. 878,284 based on PCT Application Ser. No. PCT/US85/02081, filed Oct. 22, 1985, now U.S. Pat. No. 4,699,906, which is a continuation-in-part of application Ser. No. 664,222, filed Oct. 24, 1984, now U.S. Pat. No. 4,588,719, which is a continuation-in-part of application Ser. No. 604,813, filed Apr. 27, 1984, now U.S. Pat. No. 4,638,001, which is a continuation-in-part of application Ser. No. 489,702, filed Apr. 29, 1983, now U.S. Pat. No. 4,529,723.

FIELD OF THE INVENTION

This invention relates to a class of bicyclic benzenoid compounds characterized by an ether or thioether substituent on the phenyl ring and an exocyclic nitrogen substituent on the other ring of the bicyclic ring system and methods for the treatment of physiological disorders, including gastrointestinal disorders in humans and other mammals.

REPORTED DEVELOPMENTS

Gastrointestinal hyperacid secretion, stomach and intestinal ulceration, and gastritis are major gastrointestinal disorders observed in the general adult populations of industrialized societies. Many factors, including the production of excess gastric acid and the weakening of the lining of the stomach and gastrointestinal tract against such acid are implicated as causes of these disorders. Traditional treatment of these disorders has involved the administration of antacids to neutralize the excess gastric acid and the administration of antisecretory drugs which generally reduce the production of all gastric secretions.

In the last few years, the treatment of gatrointestinal disorders such as peptic ulcer has changed to include the use of anti-secretory drugs which selectively block the production of gastric acid. These drugs are believed to interfere with the body's physiological pathway responsible for the production of gastric acid by blocking the action of histamine. Histamine production is induced in the body by a number of stimuli, including stress, allergic reaction, etc., and acts to increase gastric secretion, dilate blood vessels and stimulate smooth muscle tissue. Histamine is believed to function by way of interaction with histamine receptors in the body. The subdivision of these receptors into two groups, the $H_1$- and $H_2$-receptors, was proposed by Ash and Schild (Brit. J. Pharmacol. Chemother, 1966, 27, 427) and Black et al (Nature 1972, 236, 385). The $H_1$-receptor is involved in the bronchial and gastrointestinal smooth muscle stimulative action of histamine. Drugs which block this action are labelled "antihistamines" (e.g. mepyramine).

Black et al, cited above, described the group of substances which act at histamine receptors other than the $H_1$-receptor as the $H_2$-receptors. Blocking the action of histamine at the $H_2$-receptors will selectively block histamine's stimulative action on gastric acid secretion and heart rate. Burimamide was the first clinically effective $H_2$-receptor antagonist inhibiting gastric secretion in man; but Burimamide's oral absorptivity is poor. Subsequent studies developed the orally active Metiamide, the side effects of which limited clinical use, and Cimetidine which has been marketed as an anti-ulcer drug. A number of classes of heterocyclic chemical compounds have been reported as $H_2$-receptor antagonists, for example, those disclosed in U.S. Pat. Nos. 4,104,381, 4,279,819, 4,323,566, 4,390,701, 4,395,553, and British published patent applications Nos. GB 2067987A and GB 2047238A, and EPO publication No. 0081955A2, the disclosures of which are incorporated by reference.

Another method for the prevention or treatment of gastric ulcer comprises the use of drugs which neither neutralize nor inhibit the secretion of gastric acid. These drugs constitute a class of anti-ulcer compounds which function to enhance the normal defense mechanisms of the body, rather than to reduce normal body secretions, and are described as "cytoprotective" agents. It has been proposed that such agents act to strengthen the mucosal lining of the gastrointestinal system by one or more mechanisms, thereby preventing any damage which could result from the action of strong gastric acid. Prostaglandins have been implicated in the mechanism of cytoprotection by a number of workers in the field. See, the discussion of cytoprotection in Robert, Andre, "Prostaglandin and Digestive Diseases", *Advances in Prostaglandin and Thromboxane Research*, Vol. 8 (Raven Press, N.Y. 1980), and Robert et al, "Cytoprotection by Prostaglandins in Rats", *Gastroenterology*, 77, 433–443 (1979), hereby incorporated by reference. Drugs, other than prostaglandins, which exhibit cytoprotective activity include carbenoxolone sodium, reported to exhibit undesirable side effects, such as edema, diastolic hypertension or hypokalemia, and the thiazol-2-yl-carbamoylcarboxylic acids, esters and imides described in U.S. Pat. No. 4,321,372.

Compounds of the present invention comprise bicyclic benzenoids which exhibit anti-secretory activity, $H_2$-receptor antagonist activity, anti-ulcer activity and cytoprotective activity.

SUMMARY OF THE INVENTION

This invention comprises a class of compounds according to Formula I

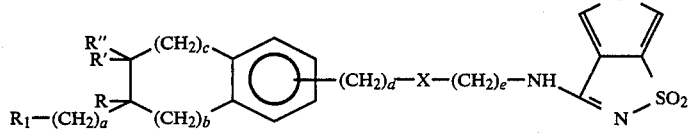

Formula I wherein:
a is 0, 1 or 2;
b is 0 or 1;
c is 0, 1-b, 2-b or 3-b;
d is 0 or 1;
e is 2, 3 or 4;
X is oxygen, sulfur,

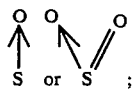

R, R' and R'' are each independently H, alkyl, or aralkyl;

$R_1$ is —$NR_2R_3$, or

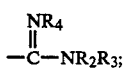

$R_2$ and $R_3$ are each independently H or alkyl, or both together with the nitrogen to which they are attached form a 5, 6 or 7-membered ring which may include one to three additional hetero atoms of N, O or S;

$R_4$ is H or lower alkyl or $R_4$ together with $R_2$ are ethylene or propylene and form a 5 or 6 membered ring with the nitrogen atoms to which they are attached;

or a pharmaceutically acceptable salt thereof.

Compounds within the scope of Formula I exhibit physiological activity in mammals including anti-secretory activity, histamine $H_2$-receptor antagonist activity, anti-ulcer activity and cytoprotective activity.

Another aspect of this invention relates to the class of geometric isomeric compounds according to Formula I, which class of compounds exhibits an unexpected and surprising level of physiological activity including anti-secretory, histamine $H_2$-receptor antagonist and anti-ulcer activity.

This invention also relates to methods for the treatment and prevention of gastrointestinal hyperacidity and ulcerogenic disorders in humans and other mammals comprising administering to a patient an effective amount of a compound within the description of Formula I.

DETAILED DESCRIPTION OF THE INVENTION

Preferred classes of compounds according to this invention are described by Formulae II, III, IV, and V.

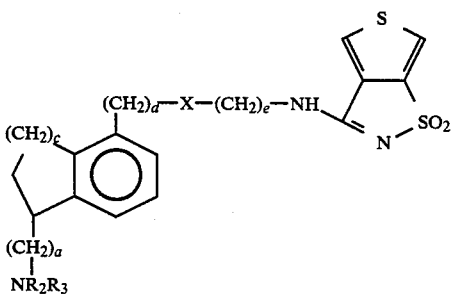

Formula II or;

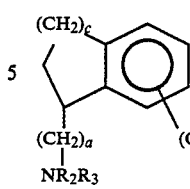

Formula III wherein:
a is 0, 1 or 2;
c is 0, 1, 2 or 3;
d is 0 or 1;
e is 2, 3 or 4;
X is oxygen or sulfur;
$R_2$ and $R_3$ are as described above.

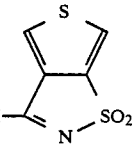

Formula IV

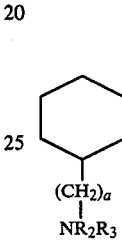

or;

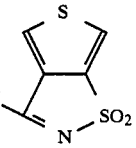

Formula V

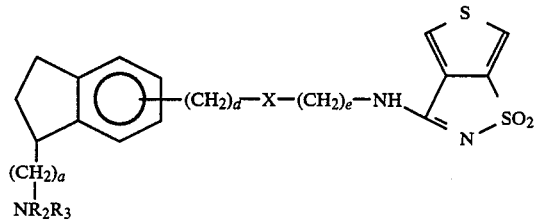

wherein:
a is 0, 1 or 2;
d is 0 or 1;
e is 2, 3 or 4;
X is oxygen or sulfur;
$R_2$ and $R_3$ are as described above.

A more preferred class of compounds within the scope of Formula I comprises the compounds of Formula I wherein:
a is 0 or 1;
b is 0;
c is 1, 2 or 3;
d is 0;
e is 3; and
X is oxygen.

A preferred subclass of compounds is described by Formula IV or V, wherein:
a is 0 or 1;
d is 0;
e is 3; and
X is oxygen.

Another more preferred subclass of compounds is described by Formula IV or V, wherein:
a is 0 or 1;
d is 1;
e is 2; and X is sulfur.

A particularly interesting class of compounds according to Formula IV or V comprises those compounds wherein $R_1$ is 1-piperidinyl, 1-pyrrolidinyl, 1-morpholinyl or 1-azepinyl.

The compounds of Formulae I to V may also form hydrates and exhibit tautomerism. Formulae I to V are intended to encompass all hydrates and tautomers, as well as any diastereomers and optical enantiomers.

As employed above and throughout the disclosure, the following terms, unless otherwise indicated, shall be understood to have the following meanings:

"Alkyl" means a saturated aliphatic chain, either branched or straight, including up to about 22 carbon atoms.

"Lower alkyl" means an alkyl group as above, having 1 to about 6 carbon atoms. Examples of lower alkyl groups are methyl, ethyl, n-propyl, isopropyl, butyl, sec-butyl, and tert-butyl.

"Alkenyl" means an unsaturated aliphatic chain, either branched or straight, including up to about 22 carbon atoms and one or two carbon-carbon double bonds.

"Lower alkenyl" groups are preferred and include about one to about six carbon atoms and one double bond.

"Cycloloweralkyl" means an aliphatic carbocyclic radical including from about three to about seven carbon atoms in the ring. Examples include cyclopentyl, cyclohexyl, cycloheptyl and cyclobutyl.

"5, 6 or 7 membered heterocyclic ring" means a nitrogen-containing ring of the formula

where Y is alkylene or alkylidinyl having from one to six carbon atoms, and may include one to three atoms of N, O or S. Exemplary heterocyclic groups include piperidinyl, pyrrolidinyl, morpholinyl, azepinyl, pyrrolyl, imidazolyl, pyrazolyl, and thiamorpholinyl.

"Heteroaryl" means a five or six membered monocyclic ring or 9 or 10 membered bicyclic ring either of which may contain one or more heteroatoms of nitrogen, oxygen or sulfur, including furyl, pyridyl, thiazolyl, quinolinyl, indolyl or thienyl.

"Aryl" means an aromatic hydrocarbon radical group such as phenyl, tolyl, quinolyl, pyridyl, and includes phenyl, tolyl, quinolyl or pyridyl substituted by one or more substituent groups including lower alkyl, halo, carboxyl, amino, amido, hydroxyl, nitro, cyano, or sulfonyl. Preferred aryl groups include phenyl and tolyl.

"Aralkyl" means an alkyl group in which one or more hydrogens is substituted by an aryl group as above. Preferred are "arloweralkyl" groups including substituted and unsubstituted phenyl lower alkyl such as benzyl and phenethyl.

The compounds of this invention may be prepared by one of the following general synthetic schemes.

When the bicyclic benzenoid portion of the compound is directly attached to the X component of Formula I, these compounds may be prepared from a bicyclic phenolic (or phenylmercaptan) intermediate shown by Formula VI below.

One means of obtaining the appropriately substituted phenolic (or thiol) intermediate of Formula VI is illustrated in Scheme I. The starting material may be a bicyclic ketone having an oxy or mercaptyl substituent in any one of the four positions possible on the phenyl ring. The ketone can either be obtained from a commercially available source or prepared according to standard procedures known in the art.

The ketone is then converted to the enamine using a primary or secondary amine in the presence of acid, preferably a Lewis acid such as titanium tetrachloride. Any polar aprotic solvent may be used in this reaction, for example, toluene or methylene chloride.

The resulting enamine is reduced, preferably using a hydride reagent such as a borohydride. Sodium cyanoborohydride is one preferred reducing agent.

The phenolic protecting group is then cleaved to obtain the intermediate of Formula VI.

Scheme I

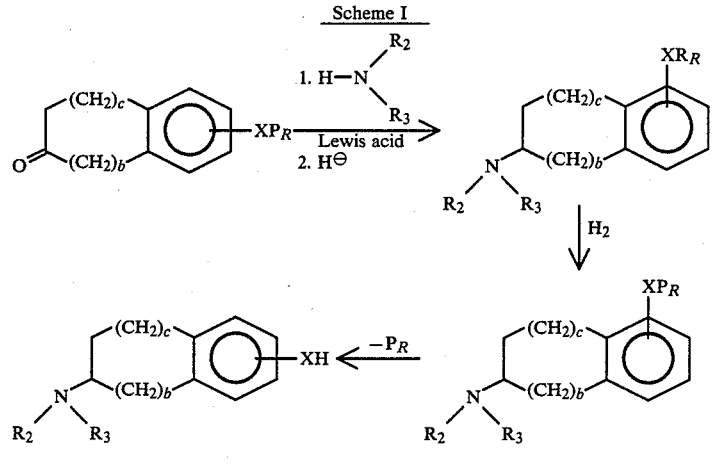

The protecting group, $P_R$, may be methyl, benzyl or the N-phthalimido alkyl. If the protecting group is chosen to be other than the N-phthalimido alkyl, the protecting group is removed according to methods known in the art. If the protecting group is N-phthalimido alkyl, then it can remain on the synthetic intermediate preceding VI and used as in the subsequent reaction step.

The formation of the ether linkage from VI is accomplished by treating the phenolic compound with a protected N-propylbromide in the presence of a base such as sodium methoxide, potassium t-butoxide or potassium carbonate. Ether coupling reagents other than a base and a bromide may also be used. (Scheme II)

group is removed with hydrazine hydrate. (Scheme III)

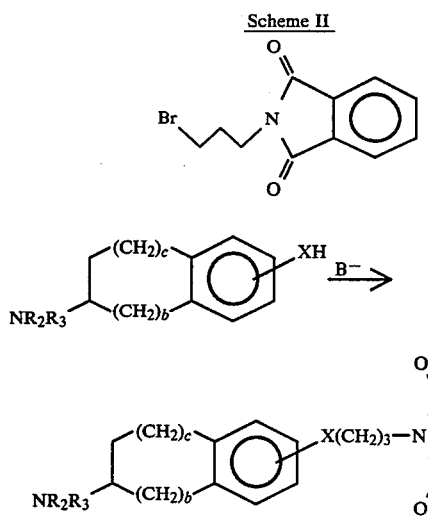

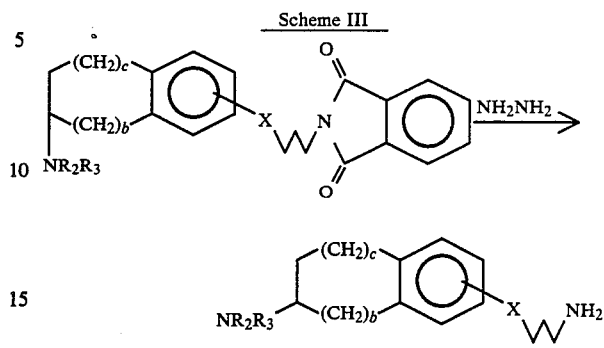

An alternate route to compounds of Formula VI above involves the reduction of the ketonic phenol, followed by the halogenation of the resulting hydroxy compound and the substitution of the desired amino group for the halo group. Scheme IV below depicts this reaction sequence showing exemplary reagents to effect the desired reactions.

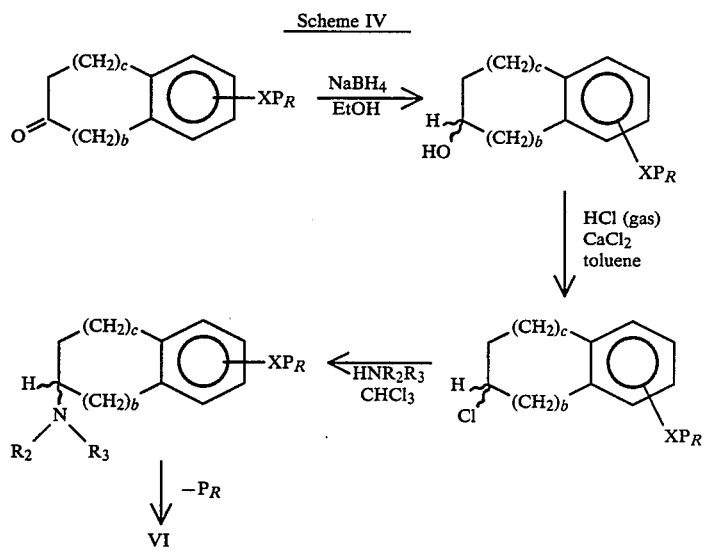

The nitrogen protecting group is preferably phthalimido but can be any protecting group insensitive to the ether formation reaction conditions, such as a base insensitive group.

The amine compound is obtained by the removal of the protecting group, for example, the phthalimido An alternate route for the formation of the ether linkage from VI involves the base catalyzed reaction of the phenolic compound with an α,ω-dihaloalkyl reagent followed by the nucleophilic displacement of the ω-halo substitutent by azide and the reduction of the azido functionality to the amine. Scheme V depicts the alternate "azide" route.

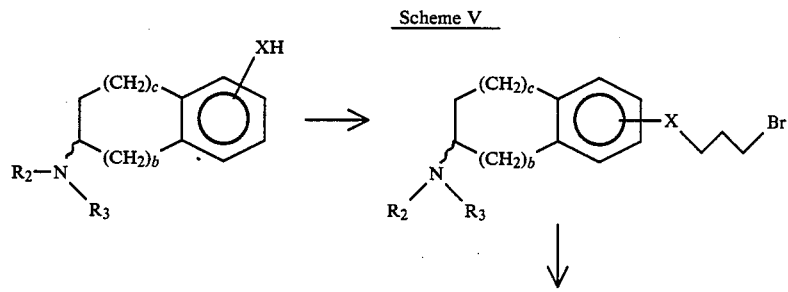

-continued

Scheme V

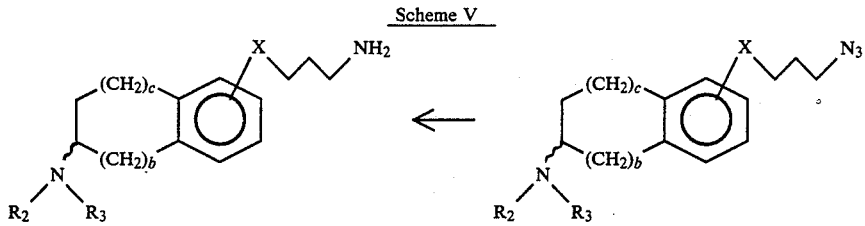

Compounds within the scope of Formula I and having a methyleneoxy or methylenethioxy substituent (d=1) on the phenyl portion of the compound may be prepared by one of the reaction sequences described below.

The methyleneoxy or methylenethio ether may be prepared from the coupling of a 2-bromoethylene phthalimide in the presence of base or 2-thioethylamine, respectively, with the methylene hydroxy compound. Scheme VI illustrates the formation of the methylenethio ether.

Scheme VI

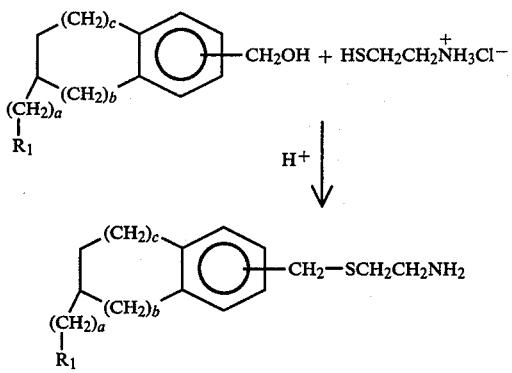

The methyleneoxy compound may be obtained by the reduction of a phenyl carboxylic acid or ester precursor such as IX. The reduction may be conducted by hydrogenation over a rhenium catalyst, by a hydride in the presence of a Lewis acid or by acidic electrolysis and depending on choice of conditions may take place before or after the formation of the amine.

Formula VII

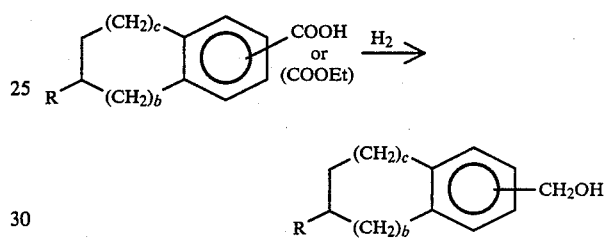

If the reduction to the methylene hydroxy compound occurs after the formation of the amine, the carboxylic acid intermediate is prepared analogously to the phenolic intermediate VI, with the acid being protected by its ester where appropriate.

Compounds within the scope of Formula I, where a is greater than zero, may be prepared by the addition of one or more carbon units at the keto-position of the starting bicyclic ketone compound as shown in Scheme VII.

Scheme VII

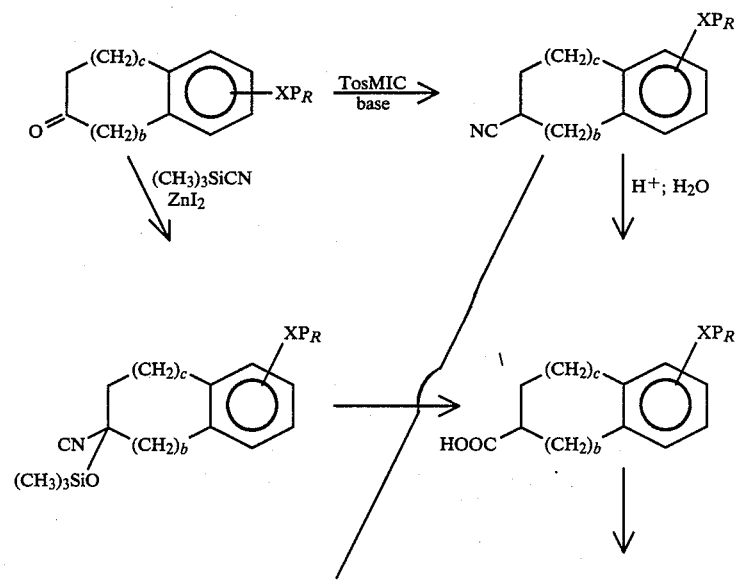

Scheme VII -continued

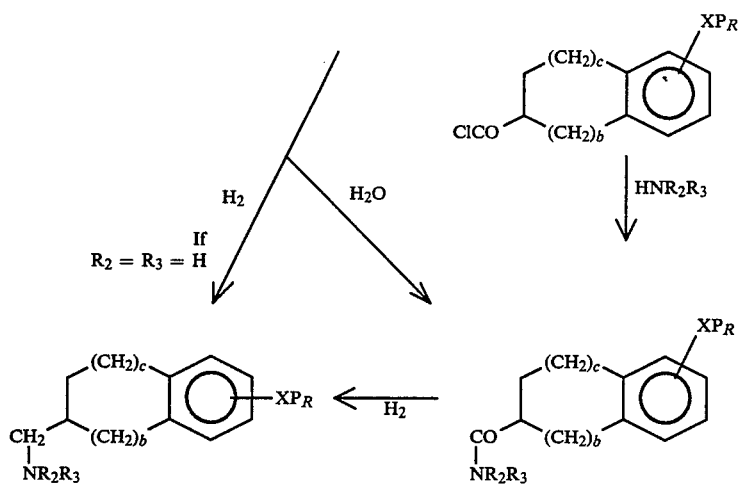

Treatment of the bicyclic ketone with trimethylsilylcyanide and zinc iodide forms the cyano trimethylsiloxy adduct in good yield. Treatment of the siloxy compound with a mixture of a Lewis acid such as tin$^{II}$ chloride and a concentrated halogenic acid such as conc. HCl in glacial acetic acid results in the formation of the carboxylic acid derivative. (See, J. L. Belletire et al, Synth. Commun. 12, No. 10, 763–70 (1982)). An alternative pathway to the carboxylic acid compound which also provides a pathway to amido and amidino derivatives is effected by the use of tosylmethylisocyanide in the presence of base. For a complete discussion of the one-step conversion of the ketone to the cyano derivative, see O. H. Oldenziel et al, J. Org. Chem., Vol. 42, No. 19, 3114–3117 (1977). The most preferred base is tert-butoxide in a non-polar aprotic solvent such as dimethylsulfoxide or HMPT. The resulting cyano compound may be hydrolyzed to the acid by means of aqueous base, for example, aqueous sodium hydroxide, or it may be hydrolyzed to the carbamoyl derivative by acidic means including, for exampl, BF$_3$ in glacial acetic acid or aqueous hydrochloric acid. The mono- or di-substituted amide may be formed by the reaction of the acyl chloride, prepared by treating the acid with SOCl$_2$ with a primary or secondary amine, i.e., HNR$_2$R$_3$. The amide may also be formed directly by a condensation reaction of the acid and amine or through the ester by amide-ester interchange.

Reduction of the amide results in the methylene amine. A hydride reducing agent such as LiAlH$_4$ in diethyl ether or tetrahydrofuran is preferred. Other reagents which may be used include LiAlH$_4$ and AlCl$_3$ in an ether solvent, boron tetrafluoride etherate in methylene chloride followed by sodium borohydride in ethanol, and diborane in tetrahydrofuran. These reagents may also be used to obtain the amine directly from the cyano intermediate. The preferred reagent is LiAlH$_4$. The amine obtained from the reduction of the nitrile may be alkylated to form the mono-, di- or cyclized derivative using the appropriate alkylating agent, such as an alkyl iodide, alkyl triflate or 1,4-dihalo-, 1,5-dihalo-, or 1,6-dihalo-alkyl compound. The pyrrolidinyl, 1-piperidinyl, morpholinyl and azepinyl compounds may be prepared by alkylating the amine with the appropriate reagents, for example, 1,4-dibromobutane or 1,5-dibromopentane.

The amidino derivatives may be prepared from the cyano intermediate. Treatment with anhydrous ethanolic hydrochloric acid forms the ethoxy iminium salt which forms the amidine upon treatment with a primary or secondary amine as depicted in Scheme VIII.

Scheme VIII

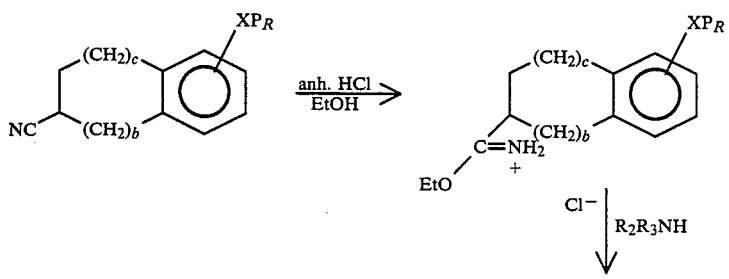

Scheme VIII

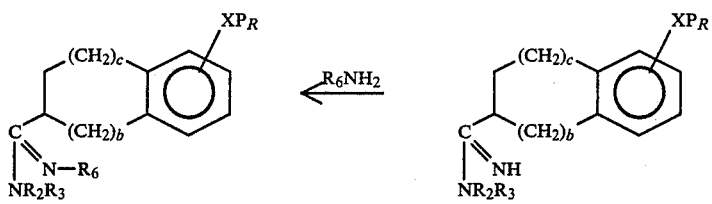

The ethylene amino and higher alkylene amino compounds according to Formula I may be prepared via the carboxylic acid intermediate by one or more alkylene chain extending reactions as shown, for example, in Scheme IX.

Scheme IX

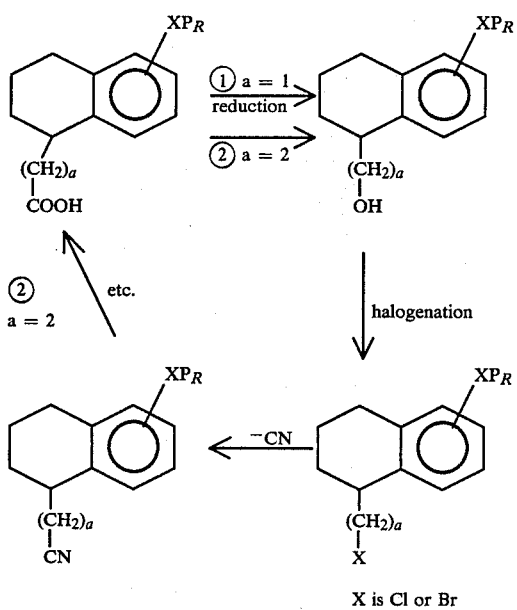

X is Cl or Br

Reduction of the carboxylic acid, shown in Scheme IX, with a hydride such as diborane is followed by the conversion of the resultant hydroxy compound into the halo derivative with a halogenation reagent such as either $SOCl_2$ or $PBr_3$. The chain-extended cyano compound is generated by treatment of the halo derivative with a cyanide and either can be converted into the amide, amine or guanidine as described above, or the chain extension process can be continued by conversion via the carboxylic acid.

Another process for the preparation of compounds within Formula I wherein a is greater than zero, comprises the formation of spiro cyclic ether intermediate by the reaction of an alkylidinyl reagent with a cyclic ketone starting material. See Scheme X, below. Rupture of the oxygen containing ring is effected with a nucleophilic nitrogen reagent $H-NR_2R_3$. The tertiary hydroxy group is removed via dehydration. Hydrogenation of the unsaturated product is followed by elaboration of the phenolic side chain as discussed herein above.

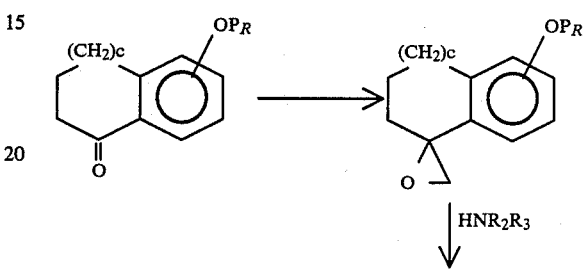

The addition of the terminal thiophenyl saccharin moiety,

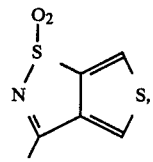

comprises treating the 3-aminoalkoxy intermediates with the 3-methyl mercaptyl-thieno[3,4]-disothiazole-1,1-dioxide reagent derivative formed from the 3-oxo-precursor, which is described in the *Journal of Organic Chemistry*, Vol. 45, 617 (1980), hereby incorporated by reference. Upon treatment of the oxo-precursor with $P_2S_5$ in pyridine, the 3-thione analog is formed, which in turn forms the methyl mercaptan compound on treatment with base and methyl iodide. See, also, the reaction sequences disclosed in U.S. Pat. No. 4,490,527, hereby incorporated by reference.

The compounds of this invention may be readily converted to their non-toxic acid addition salts by customary methods in the art. The non-toxic salts of this invention are those salts the acid component of which is pharmacologically acceptable in the intended dosages, including those prepared from inorganic acids such as hydrochloric acid, hydrobromic acid, sulfuric acid, nitric acid and phosphoric acid, and from organic acids such as methane sulfonic acid, benzenesulfonic acid, acetic acid, propionic acid, malic acid, oxalic acid, succinic acid, glycolic acid, lactic acid, salicyclic acid, benzoic acid, nicotinic acid, phthalic acid, stearic acid, oleic acid, abietic acid, etc.

The following is a selected example of the preparation of the compounds according to this invention.

EXAMPLE I

THE PREPARATION OF 3-[3-(4-[1-PIPERIDINYLINDANYLOXY]-PROPYLAMINO)]-THIENO[3,4-d]ISOTHIAZOLE-1,1-DIOXIDE

Step 1

4-Methoxy-1-indanone

Methyl iodide (69 ml) is added dropwise over a period of 15 minutes to a stirred mixture of 4-hydroxy-1-indanone (150 g) and anhydrous potassium carbonate (154 g) dissolved in DMF (1.5 liter) cooled to 0° C. under nitrogen. The reaction mixture is stirred at RT for 24 hours and partitioned between methylene chloride and water. The methylene chloride fraction is washed with water and 2% aqueous NaOH and dried over $Na_2SO_4$. The dried extract is filtered, concentrated in vacuo and the residue dissolved in hot methanol which upon cooling forms a precipitate. The precipitate is filtered and recrystallized from methanol yielding the methoxy product as a solid, M.P. 104°–106° C.

Step 2

1-Hydroxy-4-methoxyindan

Sodium borohydride (9.65 g) is added over a period of 15 minutes to a stirred suspension of 4-methoxy-1-indanone (127.3 g) in ethanol (650 ml) at a temperature of 24° C. under nitrogen. The reaction mixture is refluxed for 2 hours, cooled and glacial acetic acid (15 ml) added. The resulting mixture is concentrated in vacuo and the residue partitioned between ether and water. The ether extract is washed with water, saturated sodium bicarbonate, saturated salt, dried over $Na_2SO_4$, filtered and concentrated in vacuo yielding the hydroxy compound as a solid, M.P. 77.5°–79.5° C.

Step 3

1-Chloro-4-methoxyindan

Anhydrous hydrogen chloride is bubbled for 3 hours into a stirred mixture of 1-hydroxy-4-methoxyindan (117.9 g), calcium chloride (120 g, 4–20 mesh), and anhydrous toluene (2 l). The reaction mixture is decanted and filtered and the filtrate and supernatant evaporated yielding a brown oil which is used in the next step without further purification.

Step 4

4-Methoxy-1-piperidinylidan

A solution of 1-chloro-4-methoxyindan (from Step 3) in chloroform (130 ml) is added over a period of ten minutes to a stirred mixture of piperidine (284 ml) in chloroform (400 ml) under nitrogen. The reaction mixture is heated to reflux for six hours and allowed to stand at RT overnight. The mixture is treated with 10% aqueous HCl and the organic layer separated. The aqueous layer is extracted with methylene chloride and the combined organic extracts washed with 10% aqueous HCl. The organic layer is evaporated in vacuo and the residue partitioned between 5% aqueous HCl and ether. The combind aqueous fraction is washed with ether, made alkaline, and the alkaline layer extracted with ether. The ether extract is washed, dried and concentrated in vacuo yielding the piperidine indan as an oil.

Step 5

4-Hydroxy-1-piperidinylindan

Hydrobromic acid (47–49%, 750 ml) is added to a stirred solution of the 4-methoxy-1-piperidinylindan (75 g) in glacial acetic acid (750 ml) under nitrogen. The mixture is refluxed for four hours, allowed to cool and poured into crushed ice and water. The pH of the ice mixture is adjusted to about 9 and the aqueous mixture extracted with methylene chloride. The methylene chloride extract is washed with water thereby forming a precipitate which is filtered and the solid dried. The methylene chloride layer is evaporated yielding an oil. The solid is dissolved in acetonitrile and treated with charcoal. The oil is treated with charcoal and dissolved in acetonitrile. Both dissolved materials are recrystallized from acetonitrile yielding the desired product, M.P. 134.5°–136.5° C.

Step 6

4-(3-Bromopropyl)-1-piperidinylindan

Potassium hydroxide (53 g, 87%) is added over a period of 1 hour 15 min to a stirred suspension of 4-hydroxy-1-piperidinylindan (30 g), and tetrabutylammonium chloride (4.1 g) in 1,3-dibromopropane (140 ml) and the resulting mixture stirred at RT under nitrogen for two hours. The reaction mixture is partitioned between ice-water and ether and the aqueous layer separated and extracted with ether. The combined organic extracts are washed with water and ice cold 5% aqueous HCl forming a precipitate which is filtered and washed with ether. The acidic fraction is made strongly alkaline forming an oil precipitate which is extracted into ether. The combined ether layers are washed, dried over $Na_2SO_4$, filtered and concentrated in vacuo yielding the desired product as an oil which is used in the next step without further treatment.

Step 7

4-(3-Azidopropoxy)-1-piperidinylindan

Sodium azide (7.84 g) is added to a stirred solution of 3-bromopropoxy-1-piperidinylindan (40 g from Step 6 above) in ethanol/water (800 ml/80 ml) and the mixture heated to reflux for 24 hours. The reaction mixture is partitioned between water and methylene chloride and the organic layer separated, washed, dried, filtered and evaporated in vacuo yielding the desired azide indan as an oil.

Step 8

4-(3-Aminopropoxy)-1-piperidinylindan

A solution of the azido indan (38 g) (of Step 7 above) in ether (250 ml) is added over a period of 30 min to a suspension of LAH in anhydrous ether (1.5 l) stirred under nitrogen. The mixture is refluxed for about 1.5 hours then cooled and 6 ml $H_2O$ added. Aqueous NaOH (15% solution, 6 ml) is added followed by $H_2O$ (18 ml) and stirring continued for about 1.5 hours. The reaction mixture is filtered, the solid washed with ether and the filtrate dried over $Na_2SO_4$, filtered and concentrated in vacuo. The residue is dissolved in methylene chloride, dried, filtered and evaporated yielding the desired product as an oil.

Step 9

3-[3-(4-[1-Piperidinylindanyloxy]-propylamino)]-thieno[3,4-d]isothiazol-1,1-dioxide A suspension of 3-methylmercaptyl-thieno[3,4-d]isothiazole-1,1-dioxide (460 mg) in absolute ethanol (10 ml) is added to a solution of 4-(3-aminopropoxy)-1-(1-piperidinyl)indan (575 mg) and the reaction mixture refluxed under nitrogen overnight. The reaction mixture is cooled in an ice bath and the resulting precipitate filtered, dried, and recrystallized from ethanol, affording the desired product, M.P. 195°–197° C. (dec).

Other compounds within the scope of Formula I may be prepared utilizing the 3-methylmercaptyl-thieno[3,4-d]isothiazole-1,1-dioxide reagent as a coupling agent in conjunction with the amino intermediates analogous to 4-(3-aminopropoxy)-1-(1-piperidinyl)indan described above. The preparation of these intermediates is described above and in published PCT Application Ser. Nos. PCT/US84/00656 and PCT/US85/00789, hereby incorporated by reference. The preparation of another intermediate is described below.

EXAMPLE II

THE PREPARATION OF THE INTERMEDIATE, 4-(3-AMINOPROPOXY)-2,2-DIMETHYL-1-(1-PIPERIDINYL)INDAN

Step 1

2,2-Dimethyl-4-methoxyindanone

4-Hydroxy-indanone (25 g) is added portionwise to a stirred suspension of sodium hydride (40.1 g, 60% in mineral oil) and methyl iodide (62.4 g) in anhydrous THF (990 ml) under nitrogen and the mixture is stirred at RT overnight. The reaction mixture is quenched with $H_2O$, washed with diethyl ether and the etheral layer is washed with 10% aq. $NaHSO_3$ and $H_2O$, dried, filtered, and evaporated. The residue is chromatographed (silica gel; eluent=hexane/EtOAC) affording the desired product as a solid.

Step 2

2,2-Dimethyl-1-hydroxy-4-methoxyindan

A solution of 2,2-dimethyl-4-methoxyindanone (13.7 g) in anhydrous diethyl ether (575 ml) is added dropwise to a stirred suspension of LAH (2.87 g) in anhydrous diethyl ether (575 ml) and the mixture is refluxed under nitrogen for two hours. The reaction mixture is quenched with $H_2O$, 15% aq. NaOH and $H_2O$, stirred overnight, filtered and the filtrate evaporated in vacuo affording the desired compound as a solid.

Step 3

2,2-Dimethyl-1-(1-piperidinyl)-4-methoxyindan

Triethylamine (10 ml) is added to a stirred solution of the 1-hydroxy indane of Step 2 above (8.4 g) in methylene chloride (190 ml) at RT under nitrogen; the mixture is cooled to 0° C. and methanesulfonyl chloride (4 ml) is added. The mixture is stirred for three hours at RT, cooled to 0° C., piperidine (128 ml) added and stirred at RT overnight. Sat'd aq. sodium bicarbonate is added to the mixture and the organic phase separated, washed with aq. sodium bicarbonate, sat'd NaCl, dried, filtered and the filtrate evaporated in vacuo affording the desired product as an oil.

Step 4

2,2-Dimethyl-4-hydroxy-1-(1-piperidinyl)indan

A mixture of the 4-methoxy compound from Step 3 above (5 g) and 48% aq. HBr (50 ml) in glacial acetic acid (50 ml) is refluxed for three hours. The mixture is poured into $H_2O$, the pH added to 8–10 and extracted with methylene chloride. The organic extract is washed with sat'd NaCl, dried, filtered, evaporated and the residue chromatographed (silica gel, hexane/ether) affording the desired product as a green solid.

Step 5

4-(3-Bromopropoxy)-2,2-dimethyl-1-(1-piperidinyl)indan

Potassium hydroxide (1.44 g) is added to a stirred solution of the 4-hydroxy compound of Step 4 above (5 g) in methylene chloride (44 ml) and stirring is continued under $N_2$ for 30 min. 1,3-Dibromopropane (20.7 ml) and tetrabutyl ammonium chloride (0.63 g) are added and the mixture is stirred at RT for about 70 hours. The reaction mixture is diluted with methylene chloride, washed with $H_2O$, dried, filtered and the filtrate evaporated in vacuo. The residue is chromatographed (silica gel, hexane/ether) affording the purified desired product as an oil.

Step 6

4-(3-Azopropoxy)-2,2-dimethyl-1-(1-piperidinyl)indan

Sodium azide (1.04 g) is added to a solution of the 4-(3-bromopropoxy) compound of Step 5 above (5.9 g) in a mixture of $H_2O$ (6 ml) and ethanol (60 ml) and the reaction mixture is refluxed overnight. The mixture is poured into $H_2O$, extracted with diethyl ether and the organic extract is washed with sat'd aq. NaCl, dried, filtered and evaporated in vacuo affording the crude product as an oil.

Step 7

4-(3-Aminopropoxy)-2,2-dimethyl-1-(1-piperidinyl)indan

A solution of the 4-(3-azopropoxy) compound of Step 6 above (4.2 g) in anhydrous THF (15 ml) is added dropwise to a stirred suspension of LAH (0.65 g) in anhydrous diethyl ether (134 ml) and the mixture is refluxed under $N_2$ for two hours. The reaction mixture is quenched with $H_2O$, 15% NaOH and $H_2O$, filtered, dried and the filtrate evaporated in vacuo. The residue is chromatographed (silica gel, MeOH) affording the desired product as an oil.

Various tests in animals have been carried out to show the ability of the compounds of this invention to exhibit pharmacological responses that can be correlated with activity in humans. These tests involve such factors as the effect of the compounds of Formula I on gastric secretion and their $H_2$ antagonist and cytoprotective activity. It has been found that the compounds of this invention when tested in the above variety of situations show a marked activity.

One such test is the gastric secretion test. This test is carried out as follows: Shay rats are fasted for 4–8 hours, and water is given ad lib. The rats are selected at random and separated into groups of 10. The animals are treated intraduodenally (I.D.) with the test compounds or the vehicle immediately subsequent to the ligation of the stomach at the pyloric sphincter. The animals are sacrificed with chloroform at 4 hours post-drug administration, the stomach removed and its contents assayed for volume, pH and total acids.

A second gastric secretion test is carried out on the dog. This is outlined in the *Handbook of Physiology*, Section 6: Alimentary Canal, Volume II: Secretion. American Physiology Society, Washington, D.C., 1967.

It has been found that the compounds of this invention, when subjected to the above gastric secretion tests, display marked ability to decrease gastric volume and gastric acidity. These tests are known to correlate well will gastric activity in humans and are standard tests used to determine anti-secretory properties.

The compounds of Formula I have been found to be histamine $H_2$-receptor antagonists by the results obtained in the following $H_2$-antagonist tests.

A. Isolated Guinea Pig Atria

The $H_2$-receptor antagonist activity of the compounds of Formula I is measured by observing the beat rate response versus compound concentration in isolated guinea pig atria. A discussion of criteria to evaluate these dose-response curves may be found in, E. J. Ariens, G. A. J. vanOs, A. M. Simonis, and T. M. van Rossum, "A Molecular Approach to General Pharmacology", Sections 11A, 11B, and 111, *Molecular Pharmacology: The Mode of Action of Biologically Active Compound.* Vol. 1, Academic Press (1964).

1. Tissue Bath

A fifty ml jacketed tissue bath is maintained at 30° C. The bath consists of a Krebs-Henseleit buffer aerated with 95% $O_2$-5% $CO_2$, (pH 7.4). The buffer is prepared by mixing: 4 ml of an aqueous (distilled deionized) solution of $CaCl_2.2H_2O$ (0.37 g/ml); 4 ml of an aqueous (distilled deionized) solution of $MgSO_4.7H_2O$ (0.29 g/ml); 7.2 g of glucose; and, 2 liters of aqueous (distilled deionized) solution containing NaCl (28 g), $NaHCO_3$ (8.4 g), KCl (1.4 g) and $KH_2PO_4$ (0.6 g).

2. Preparation of Atria

Male albino guinea pigs (400–700 g, preferably 500–600 g) are killed by a blow to the back of the head and exsanguinated by cutting jugular veins and carotid arteries. The thoracic skin is opened from this neck cut and the rib cage exposed. Both sides of the rib cage and the diaphragm are cut and laid back, exposing the heart. The heart is removed by cutting through the vessels above and behind it while it is slightly elevated with forceps holding the ventricle tip. The heart is immediately placed in warm, aerated buffer and further dissected in a large petri dish of the same buffer. Since the pericardium is removed, it is possible to slip iris scissors between the atria and ventricles while holding the aorta and vessels with tweezers and cut off the atria. The atria are then dissected from any remaining tissue and vessels and suspended in the bath using small, curved taper-point needles formed into hooks and tied to an S-shaped hook and the L-shaped lower support with 00 silk.

A Beckman Type 9308 Strain Gauge Coupler connects a Beckman cardiotachometer to a Grass FT03C strain gauge supported in a rack and pinion clamp. The upper hook of the strain gauge is placed in the edge of the left atrium and the lower hook in the tip of the right atrium. The lower support is clamped in a femur clamp and the upper hook is suspended from the strain gauge lug. The strain gauge is raised until the resting tension on the tissue is 1 gram. The tissue is allowed to stabilize for about one hour with several buffer washings and tension adjustments before the addition of the test compounds.

3. Test Procedure

A control dose-response curve using cumulative, approximately tripling doses is obtained in all three running from 0.1 to 30.0 $\mu M$ histamine (0.1, 0.3, 1.0, 3.0, etc.) In order to minimize volume changes when adding drugs to the bath, small volumes of concentrated solutions are used. It is convenient to make up a 0.5M solution and dilute it to give 50, 5 and 0.5 mM solutions.

Data recorded consists of the initial baseline rate and the stable plateau rate after each addition. Histamine is then washed out and the tissues are allowed to stabilize again near the initial baseline rate; this may take several rinses and 1 hr. The test compound is then added at the same cumulative doses and rates again recorded. If the compound behaves as an agonist and stimulates, then the dose is increased until the rate plateaus or the concentration is 1.0 mM. If, however, no agonistic activity is observed when the concentrations has reached 100 $\mu M$ then its antagonistic activity is assessed by repeating the histamine curve without washing out the test compound. Reversibility of effect is assessed by attempting to wash out the test compound and/or histamine and repeat the histamine curve. Erratic or irregular beating or any other abnormal behavior at any time is noted. Calculations consist of the change in rate from base line and that change as a percentage of the maximum rate obtained in the initial control curve. The mean of those percentages ($\pm$SEM) is plotted as a function of agonist concentration (either histamine or test compound) to evaluate the type of response.

B. Lumen Perfused Rat Stomach-Effect on the Gastric Secretion

Male Sprague-Dawley rats weighing between 350 and 500 gm are housed individually according to standard animal husbandry procedures and are deprived of food twenty-four hours prior to testing. The rats are anesthetized by an intraperitoneal injection of 25% solution of urethane (0.5 to 0.7 ml/100 g of body weight). Once anesthetized, the trachea is exposed and cannulated with PE 100 tubing. The jugular vein is exposed and cannulated with PE 50 tubing bevelled at the tip. The abdomen is opened through a midline incision, and the esophagus is isolated excluding the vagus nerve. PE 190 tubing, with a flange on one end, is passed down the rat's mouth through the esophagus and into the stomach. The esophagus is tied off and the tubing checked to make sure that it is securely in the stomach. The duodenum is then identified and a small cut made about 1 cm below the pyloric sphincter. A piece of PE 320 tubing (flanged at one end) is inserted through the cut and into the stomach. It is secured firmly by tying a ligature around the pylorus. Using a 50 ml syringe, the stomach is flushed out with 0.4 mM NaOH through the esophageal tube until the perfusate emerging from the pyloric tube is clear. The animal is placed on a tilted table covered with a Gordon-Rupp water blanket Model 'K' to maintain the rat's body temperature at 30° C. The tube going into the esophagus is attached to a Sage Peristaltic Pump and 0.4 mN NaOH (pH 10.0) is perfused and collected in 30 ml beakers. The beakers are changed every 10 or 15 minutes and the pH of these samples are recorded. Once the pH has stabilized around 6.5–7.5, drugs that affect gastric secretion are given intravenously. The effectiveness of a compound is based on its ability to prevent a drop in pH initiated by a gastric stimulant, such as histamine. See, Ghosh, M. N. and Schild, H. O., *Brit. J. Pharmacol.*, 13: 54 (1958).

Compounds within the scope of Formula I have also been determined to exhibit anti-ulcer activity. The anti-ulcer properties of these compounds can be evaluated using an anti-ulcer assay in which aspirin or another nonsteroidal anti-inflammatory agent is used to induce gastric ulcers in the rat according to the following test procedure.

See, Corell, T., "Interaction of Salicylates and other Non-steroidal Anti-inflammatory Agents in Rats as Shown by Gastro-ulcerogenic and Anti-inflammatory Activities, and Plasma Concentrations", Acta. Pharmacology et. Toxicology, 45, 225–231 (1979).

Male Sprague-Dawley rats 140–170 g are housed according to standard animal husbandry procedures. The rats are fasted twenty-four hours prior to testing. On the test day, rats are divided into groups of 5 or 10, with one group serving as controls and receiving vehicle (for example, distilled water or a 0.1% Tween 80 solution). The test compounds, using logarithmic doses, are administered at a dose volume of 10 ml/kg. Thirty minutes post-drug, the rats are orally administered (10 ml/kg) aspirin or indomethacin suspended in 0.1% Tween 80 at a dose of 150.0 or 20.0 mg/kg, respectively. Four hours following indomethacin administration (five hours after aspirin administration) animals are sacrificed via cervical dislocation; their stomachs are removed, opened along the greater curvature, and gently rinsed and examined for lesions with a 10× magnifying glass; the following scale is employed:

| Grade | Description |
|---|---|
| 0 | No lesions |
| 1 | 5 lesions, all < 2 mm |
| 2 | 5 lesions, at least 1 > 2 mm |
| 3 | 5–10 lesions, all < 2 mm |
| 4 | 5–10 lesions, at least 1 > 2 mm |
| 5 | 10 lesions, all < 2 mm |
| 6 | 10 lesions, at least 1 > 2 mm |
| 7 | Perforation |

The average ulcer severity (±S.E.) for each group of animals is calculated. The percent inhibition for each test compound is calculated as follows:

$$\% \text{ inhibition} = \frac{\text{Mean value for control} - \text{Mean value for experimental}}{\text{Mean value for control}} \times 100$$

The compounds of Formula I have also been determined to exhibit cytoprotective activity.

The cytoprotective effectiveness of the compounds of Formula I is evaluated according to the following test procedure.

Male Sprague-Dawley rats 150–200 g are housed according to standard animal husbandry procedures. The rats are fasted twenty-four hours prior to testing. On the test day, rats are divided into groups of 6, with one group serving as controls and receiving vehicle (for example, distilled water or a 0.5% Methocel solution). The test compounds, using logarithmically spaced doses, are administered at a dose volume of 5 ml/kg. Ten minutes post-drug, the rats are orally administered 1 ml of absolute alcohol, 0.2N NaOH (1 ml) or 0.6N HCl (1 ml), regardless of body weight. One hour after administration animals are sacrificed by cervical dislocation, their stomachs are removed, opened along the greater curvature, rinsed under running tap water and examined for lesions with a 2×–10× magnifying glass.

The reduction of lesion count, lesion severity score and ulcer index as compared to similar measurements made in the controls was expressed as a percentage. Measurement of statistical significance of the results was done by standard methods.

The average ulcer severity (±S.E.) for each group of animals is calculated. The percent inhibition for each test compound is calculated as follows:

$$\% \text{ inhibition} = \frac{\text{Mean value for control} - \text{Mean value for experimental}}{\text{Mean value for control}} \times 100$$

The results of the anti-secretory, anti-ulcer and cytoprotective assays, detailed above, establish the anti-secretory activity, the $H_2$-receptor antagonist activity, the anti-ulcer activity, the cytoprotective activity, and the utility of the compounds of the present invention in the treatment of peptic ulcers in mammals, including humans. These compounds both aid in the healing of such ulcers and also prevent their formation.

Certain compounds according to the present invention comprise an optically active isomeric class of compounds according to Formula I, wherein the tetrahedral carbon atom in the 1-position is in the S configuration.

It has been found that the S(+) enantiomer of a compound of Formula I possesses good histamine $H_2$-receptor antagonist activity. The separation of activity may be measured in the pharmacological tests described herein above including: the guinea pig atria test; the lumen perfused stomach test; the aspirin induced ulcer test; and the pylorus-ligated rat test.

In particular, the compounds according to Formulae I to V are useful: in the treatment and prevention of hyperacidity and gastrointestinal ulceration; for decreasing gastrointestinal acid secretion in mammals; and for enhancing the gastrointestinal resistance to gastrointestinal irritants in humans and other mammals.

For all these purposes, the compounds of this invention can be normally administered orally or parenterally. Oral administration is preferred.

The compounds according to the invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, for example, $H_1$-antagonists, or known antacids such as aluminum hydroxide, magnesium hydroxide, magnesium trisilicate, aluminum glycinate, or calcium carbonate. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, and made isotonic with sufficient saline or glucose.

The dosage regimen in carrying out the methods of this invention is that which insures maximum therapeutic response until improvement is obtained and thereafter the minimum effective level which gives relief. Thus, in general, the dosages are those that are therapeutically effective in the treatment of gastrointestinal disease conditions or symptoms, such as duodenal and peptic ulcer. In general, the dose can be between about 0.1 mg/kg and 100 mg/kg (preferably in the range of 1 to 20 mg/kg), bearing in mind, of course, that in selecting the appropriate dosage in any specific case, consideration must be given to the patient's weight, general health, age, and other factors which may influence response to the drug. The daily dose can range from 1 to 4 times a day.

We claim:

1. A compound of the formula:

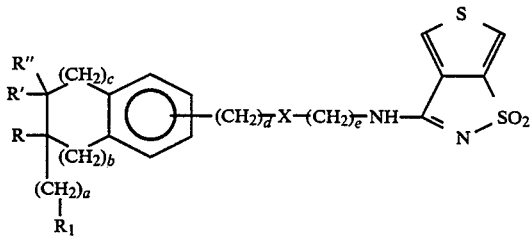

wherein:
a is 0, 1 or 2;
b is 0 or 1;
c is 0, 1-b, 2-b or 3-b;
d is 0 or 1;
e is 2, 3 or 4;
X is oxygen, sulfur,

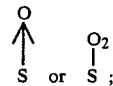

R, R' and R'' are each independently H, alkyl, or aryl-alkyl wherein aryl is phenyl or substituted phenyl $R_1$ is

$R_2$ and $R_3$ are each independently H or alkyl, or both together with the nitrogen to which they are attached form a 5, 6 or 7-membered ring which may include one to three additional hetero atoms of N, O or S; and $R_4$ is H or lower alkyl or $R_4$ and $R_2$ together are ethylene or propylene and form a 5- or 6-membered ring together with the nitrogens to which they are attached; or a pharmaceutically acceptable salt thereof.

2. A compound according to claim 1 wherein:
a is 0;
b is 0;
d is 0;
e is 3; and
X is oxygen.

3. A compound according to claim 1, wherein the carbon atom to which the $R_1—(CH_2)_a—$ group is attached is in the S(+) configuration.

4. A compound according to claim 1, wherein the carbon atom to which the $R_1—(CH_2)_a—$ group is attached is in the R— configuration.

5. A compound according to claim 1, which is the racemic mixture of the base or a pharmaceutically acceptable salt thereof.

6. A pharmaceutical composition wherein the active ingredient is a compound according to claim 1 in admixture with a pharmaceutical carrier.

7. A method for decreasing acid secretion in the gastrointestinal tract of mammals by administering thereto an anti-secretory effective amount of a compound according to claim 1.

8. A method for the treatment of gastrointestinal hyperacidity and ulceration in a mammal comprising administering thereto an effective amount of a compound according to claim 1.

9. A method for enhancing the gastrointestinal resistance to gastrointestinal irritants in humans and mammals comprising administering thereto an effective cytoprotective amount of a compound of the formula according to claim 1.

* * * * *